US00PP12260P2

(12) United States Plant Patent
Booman

(10) Patent No.: US PP12,260 P2
(45) Date of Patent: Dec. 11, 2001

(54) BEGONIA PLANT NAMED 'DENVER LACE'

(76) Inventor: James Lawrence Booman, 2302 Bautista Ave., Vista, CA (US) 92084

( * ) Notice: Subject to any disclaimer, the term of this patent is extended or adjusted under 35 U.S.C. 154(b) by 0 days.

(21) Appl. No.: 09/375,782

(22) Filed: Aug. 17, 1999

(51) Int. Cl.[7] ..... A01H 5/00
(52) U.S. Cl. ..... Plt./343

(58) Field of Search ..... Plt./343

*Primary Examiner*—Bruce Campell
*Assistant Examiner*—Anne Marie Grünberg
(74) *Attorney, Agent, or Firm*—C. A. Whealy

(57) ABSTRACT

A new and distinct cultivar of Rex Begonia plant named 'Denver Lace', characterized by its uniform growth habit; moderate plant vigor; no requirement for winter dormancy; and interesting and attractive leaf coloration and pattern.

1 Drawing Sheet

BACKGROUND OF THE INVENTION

The present invention relates to a new and distinct cultivar of Begonia plant, botanically known as *Begonia rex* hybrid, commercially known as Rex Begonia, and hereinafter referred to by the name 'Denver Lace'.

The new Rex Begonia was discovered and selected by the Inventor in a controlled environment in Vista, Calif., in 1995, within a large group of seedling progeny from multiple crossings of unidentified selections of *Begonia rex* hybrids.

The selection of this plant was based on its uniform growth habit, moderate plant vigor, salt tolerance and attractive foliage coloration and pattern.

Asexual reproduction of the new Rex Begonia by leaf cuttings taken in a controlled environment in Vista, Calif., has shown that the unique features of this new Rex Begonia are stable and reproduced true to type in successive generations.

SUMMARY OF THE INVENTION

The cultivar 'Denver Lace' has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Denver Lace'. These characteristics in combination distinguish 'Denver Lace' as a new distinct and Rex Begonia:

1. Uniform growth habit.
2. Moderate plant vigor.
3. Does not require winter dormancy.
4. Interesting and attractive leaf coloration and pattern.

In side-by-side comparisons conducted by the Inventor in Vista, Calif., plants of the new Rex Begonia differ from plants of the nonpatented cultivar Merry Christmas Corkscrew in the following characteristics:

1. Plants of the new Rex Begonia have larger and flatter leaves than plants of the cultivar Merry Christmas Corkscrew.

2. Plants of the new Rex Begonia are more vigorous than plants of the cultivar Merry Christmas Corkscrew.

3. Leaves of plants of the new Rex Begonia and the cultivar Merry Christmas Corkscrew differ in coloration and pattern.

4. Leaves of plants of the new Rex Begonia do not have a "corkscrew" formation whereas leaves of plants of the cultivar Merry Christmas Corkscrew have a "corkscrew" formation.

5. Plants of the new Rex Begonia do not require a winter dormancy period whereas plants of the cultivar Merry Christmas Corkscrew do require a winter dormancy period.

In side-by-side comparisons conducted by the Inventor in Vista, Calif., plants of the new Rex Begonia differ from plants of the nonpatented cultivar Lillium in the following characteristics:

1. Plants of the new Rex Begonia are more compact than plants of the cultivar Lillium.

2. Plants of the new Rex Begonia have larger and flatter leaves than plants of the cultivar Lillium.

3. Leaves of plants of the new Rex Begonia and the cultivar Lillium differ in coloration and pattern.

4. Plants of the new Rex Begonia do not require a winter dormancy period whereas plants of the cultivar Lillium do require a winter dormancy period.

BRIEF DESCRIPTION OF THE PHOTOGRAPH

The accompanying colored photograph illustrates the overall appearance of the new Rex Begonia, showing the colors as true as it is reasonably possible to obtain in colored reproductions of this type. The photograph comprises a top perspective view of a typical plant of 'Denver Lace'. Foliage colors in the photograph many differ from the actual colors due to light reflectance.

DETAILED BOTANICAL DESCRIPTION

In the following description, color references are made to The Royal Horticultural Society Colour Chart except where general terms of ordinary dictionary significance are used. The following observations and measurements describe plants grown during the Spring in Vista, Calif., under conditions which approximate commercial practice. Plants used for this description were grown in 15-cm containers for about 3 months.

Botanical classification: *Begonia rex* hybrid cultivar Denver Lace.

Commercial classification: Rex Begonia.

Parentage: Chance seedling of multiple crossings of unidentified selections of *Begonia rex* hybrids.

Propagation:

*Type*.—Leaf cuttings.

*Time to initiate roots, summer*.—About 56 days at 21° C.

*Time to initiate roots, winter*.—About 56 days at 21° C.

*Time to develop roots, summer*.—About 84 days at 21° C.

*Time to develop roots, winter*.—About 98 days at 21° C.

*Rooting habit*.—Fine, fibrous and well-branched.

Plant description:

*Plant form*.—Rosette; compact; outwardly arching potted plant; freely basal branching with good leaf petiole strength.

*Vigor*.—Moderate.

*Plant height, soil surface to top of leaf canopy*.—About 19 cm.

*Plant width*.—About 42 cm.

*Leaves*.—Arrangement: Simple. Length: Petiole to apex: About 13.5 cm. Base to apex: About 17 cm. Width: About 15.2 cm. Shape: Asymmetrical ovate, oblique. Apex: Acute. Base: Overlapping cordate. Margin: Pectinate; irregularly undulate. Texture: Leathery, rugose; pubescence on lower surface veins. Color: Young foliage, upper surface: Margin, central venal areas: Close to 200A with tinge of 187A; iridescent blisters of 157A, tinged with 187C; larger in center; minute spots in outer area, 146A. Young foliage, lower surface: Margin, central venal areas: Bleeding outward close to 187A. Intervenal: 148B. Mature, fully expanded, foliage, upper surface: Margin, central venal areas: Dark brown, 200A, body of leaf darker than 146A; iridescent blisters, 194B to 194C, tinged with 185B to 185C. Veins: 187A. Mature, fully expanded, foliage, lower surface: Margin, central venal area: 187A bleeding into 148B to 148C. Veins: 183A; reticulate.

*Petioles*.—Length: About 11 cm. Diameter: About 8 mm. Shape: Canaliculate. Texture: Pubescent. Color: 183A.

*Stipules*.—Length: About 1.9 cm. Diameter at base: About 1.1 cm. Shape: Deltoid. Color: Close to 179A.

Flower description:

*Flowering habit*.—Male flowers, single with one whorl of four tepals Female flowers, semi-double with three tepals. interior to outer whorl of five tepals. Usually about three or four flowers per cyme. Flowers persistent.

*Natural flowering season*.—Plants will flower continuously, but typically plants flower more abundantly during the spring and summer.

*Flowers*.—Shape: Rounded; somewhat cup-shaped. Diameter: About 4.2 cm. Depth (height): About 1.5 cm. Aspect: Drooping about 35° from vertical. Fragrance: None.

*Flower buds*.—Shape: Ovoid; bulbous with marginal lip. Length: About 1.6 cm. Diameter: About 1.2 cm. Color: 61D.

*Tepals*.—Arrangement: Rosette. Length: About 2 cm. Width: About 1.6 cm. Shape: Ovate with obtuse apex. Margin: Entire. Texture: Smooth, waxy; iridescent, translucent. Color: When opening, upper surface: 55B to 55C. When opening, lower surface: 54C; veins, 54B. Fully opened, upper surface: 62A, 55B shading to 55D at center. Fully opened, lower surface: Close to 54B; 55B shading to 55D at center.

*Peduncles*.—Angle: About 45° from vertical. Length: About 6.5 cm. Diameter: About 2.5 mm. Strength: Firm. Texture: Smooth, waxy. Color: 178B.

*Pedicels*.—Angle: About 45° from vertical. Length: About 2.6 cm. Diameter: About 1.5 mm. Strength: Moderate. Texture: Smooth, waxy. Color: 181A.

*Reproductive organs*.—Male flowers: Stamen quantity: About 68; globose mass. Anther shape: Rhomboidal; lower surfaces curved inwardly. Anther length: About 2.5 mm. Filament length: About 2.5 mm. Anther color: Close to 32A. Pollen: Not observed. Female flowers: Pistil length: About 2.8 cm. Stigma shape: Funnel; bilobate. Stigma color: 32B to 32C; margin, 9A. Ovary: Inferior; three-winged; one large top wing, 50A, and two lower wings, both surfaces 42C.

Disease resistance: Resistance to diseases common to Rex Begonia has not been determined.

Seed production: Seed production has not been observed.

It is claimed:

1. A new and distinct cultivar of Rex Begonia plant named 'Denver Lace', as illustrated and described.

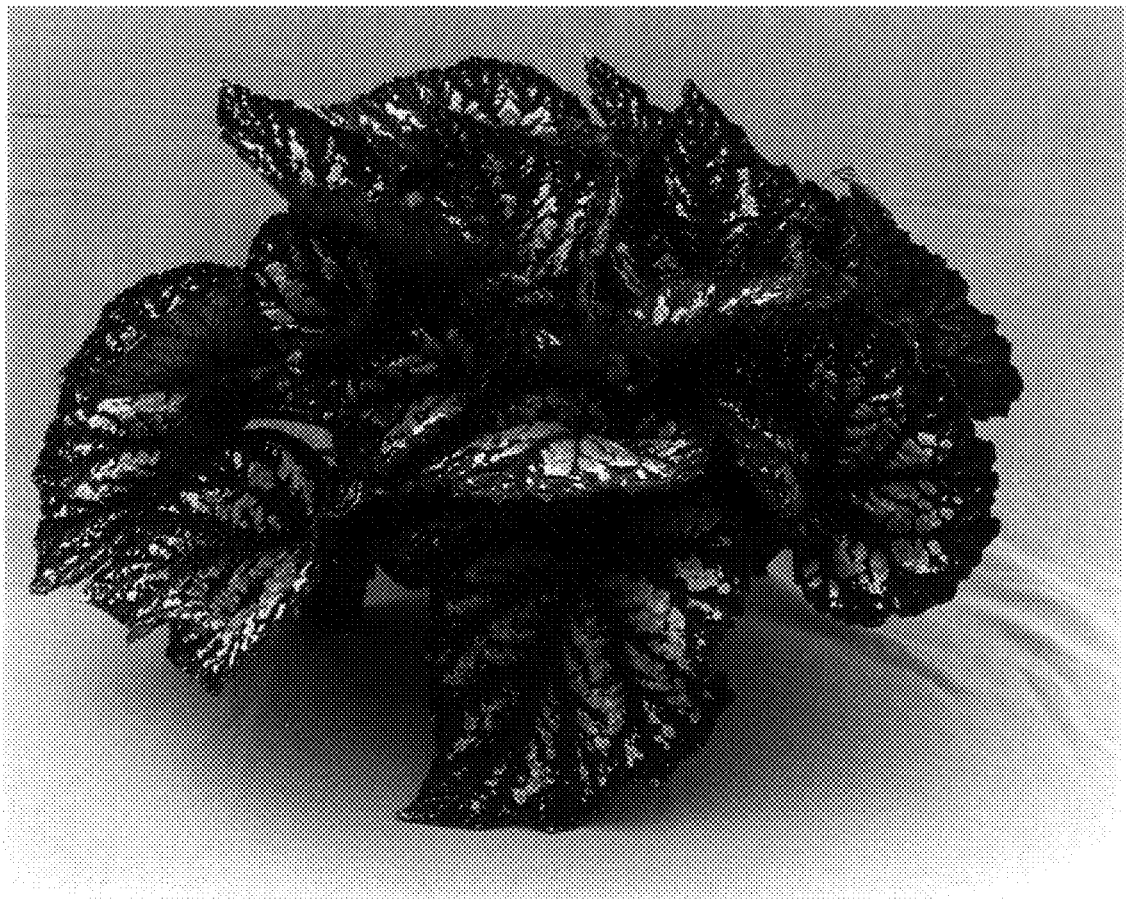

* * * * *